United States Patent [19]

Dunn et al.

[11] Patent Number: 4,570,494
[45] Date of Patent: Feb. 18, 1986

[54] APPARATUS FOR SAMPLING AND CHARACTERIZING AEROSOLS

[75] Inventors: Patrick F. Dunn, Downers Grove; Joseph E. Herceg, Naperville; Robert H. Klocksieben, Park Forest, all of Ill.

[73] Assignee: The United States of America as represented by the United States Department of Energy, Washington, D.C.

[21] Appl. No.: 599,110

[22] Filed: Apr. 11, 1984

[51] Int. Cl.[4] .............................................. G01N 1/22
[52] U.S. Cl. .............................. 73/863.22; 73/863.21; 73/863.31; 422/88
[58] Field of Search .................. 73/28, 863.21, 863.22, 73/863.31; 422/83, 86, 88

[56] References Cited

U.S. PATENT DOCUMENTS

| | | |
|---|---|---|
| 2,538,116 | 1/1951 | May ........................................ 73/28 |
| 3,127,763 | 4/1964 | Lippmann ............................... 73/28 |
| 3,668,825 | 6/1972 | McIlvaine . |
| 3,807,218 | 4/1974 | Carson . |
| 4,155,247 | 7/1979 | Kaczmarek . |
| 4,211,116 | 7/1980 | Pilat . |
| 4,321,822 | 3/1982 | Marple et al. . |
| 4,391,151 | 7/1983 | Nelson . |

Primary Examiner—S. Clement Swisher
Attorney, Agent, or Firm—Jeannette M. Walder; Robert J. Fisher; Judson R. Hightower

[57] ABSTRACT

Apparatus for sampling and characterizing aerosols having a wide particle size range at relatively low velocities may comprise a chamber having an inlet and an outlet, the chamber including: a plurality of vertically stacked, successive particle collection stages; each collection stage includes a separator plate and a channel guide mounted transverse to the separator plate, defining a labyrinthine flow path across the collection stage. An opening in each separator plate provides a path for the aerosols from one collection stage to the next. Mounted within each collection stage are one or more particle collection frames.

10 Claims, 6 Drawing Figures

APPARATUS FOR SAMPLING AND CHARACTERIZING AEROSOLS

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory. This invention was supported by the Electric Power Research Institute under Program RP 2135-5 between the Electric Power Research Institute and Argonne National Laboratory.

BACKGROUND OF THE INVENTION

This invention relates generally to apparatus for sampling and characterizing aerosols. An aerosol is a colloidal system in which a gas, frequently air, is the continuous medium, and particles of solids or liquids are dispersed in it. Aerosols are commonly studied in connection with air pollution control and environmental safety. There are numerous industrial applications requiring aerosol sampling and characterization. In a nuclear reactor, for example, failure of a water-cooled fuel pin would produce fission-product aerosols under conditions of high pressure (0.35–17.5 MPa) and temperatures (700–1900 K) in the presence of steam, hydrogen, noble-gases and fission-product vapors travelling at relatively low velocities (0.1–30 cm/s). Such aerosols (in both liquid and solid states) would include particles in the 0.01–100 $\mu$m range, number densities of $10^3$–$10^8$ particles/cm$^3$, and mass loadings up to approximately 1 g/s.

The basic methods of aerosol sampling (by particle separation) are represented by four classes of instruments: impactors, impingers, centrifugal units, and gravitational units. Commercially available devices generally fall into one of these categories using only a single collection scheme. The relative efficiency of the device depends primarily on the size of particles present and the velocity of the air stream. Each collection scheme is primarily directed to a particular range of conditions. For example, impaction is effective for particles greater than one micron, whereas diffusion is effective for particles approximately 0.1 micron and below. Inertial and centrifugal samplers may have a high power demand. High efficiency in such devices is generally associated with a marked pressure drop, requiring increased power to move the air through the sampler. Gravitational units require low velocities because the number of particles removed increases with falling speed.

Therefore, it is an object of the present invention to provide an apparatus for sampling and characterizing aerosols over a wide particle size range.

It is another object of the present invention to provide an apparatus for sampling aerosols at relatively low velocities.

It is also an object of the present invention to provide an apparatus for sampling and characterizing fission-product aerosols.

Additional objects, advantages, and novel features of the invention will be set forth in part in the description which follows, and in part will become apparent to those skilled in the art upon examination of the following or may be learned by practice of the invention.

SUMMARY OF THE INVENTION

To achieve the foregoing and other objects and in accordance with the purposes of the present invention, an apparatus for sampling aerosols may comprise: a chamber having an inlet at one end and an outlet at the other end, said chamber including: a plurality of vertically stacked, successive particle collection stages located within said chamber between said chamber inlet and chamber outlet and together with said chamber, defining a flow path from said chamber inlet, through successive collection stages, to said chamber outlet, each of said collection stages including: a separator plate located within and extending across said chamber for separating that stage from the previous stage, said separator plate having an inlet opening extending therethrough, a channel guide, mounted transverse to said separator plate, defining a labyrinthine flow path from said inlet opening to the inlet opening of the next stage, and one or more particle collection means located within said labyrinthine flow path. Preferably more than one particle collection means are used, such as collector plates for gravitational settling, fine-wire impactors, and diffusion battery screens.

BRIEF DESCRIPTION OF THE DRAWINGS

The present invention is illustrated in the accompanying drawings wherein.

DETAILED DESCRIPTION OF THE INVENTION

Figure 1:
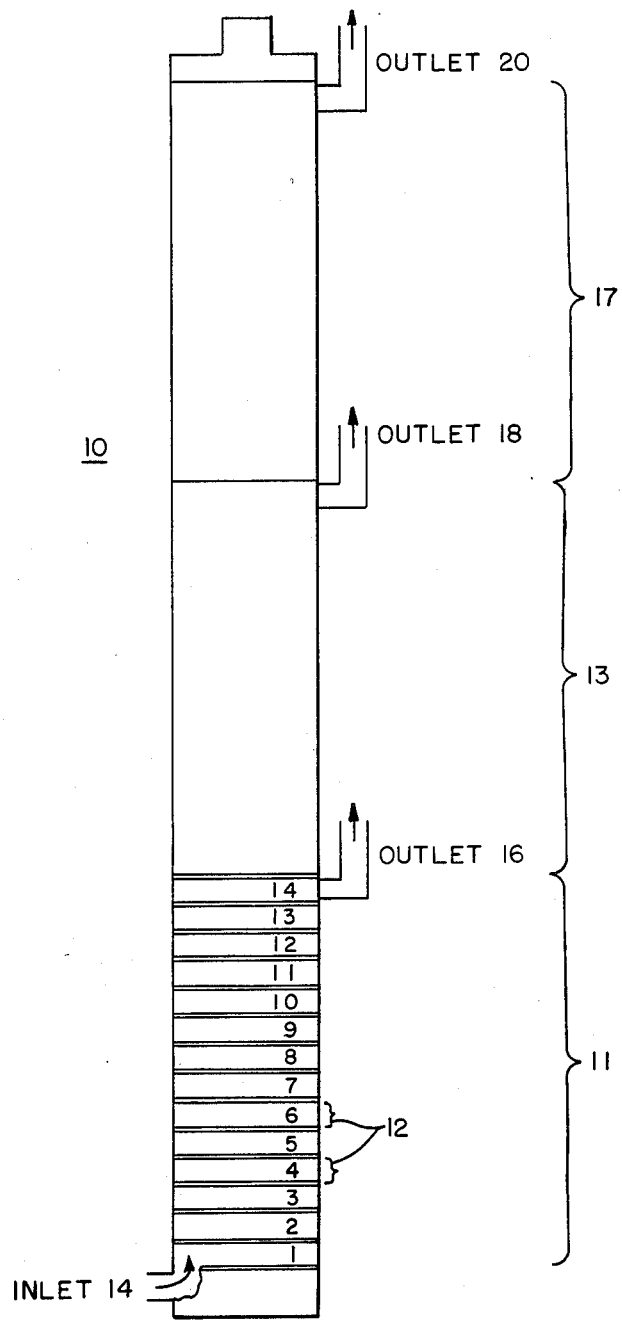
FIG. 1 is a schematic of an aerosol sampling device having three separate chambers, each chamber having fourteen collection stages.

An aerosol sampling device 10 which is actually three separate devices is shown schematically in FIG. 1. Aerosol sampling device 10 includes three chambers, 11, 13, and 17, which are stacked vertically. Each chamber contains fourteen collection stages, 12. A manifold tube (20, shown in FIG. 2) extends vertically through all three chambers transverse to and through the collection sections and is connected to inlet 14 which is connected to the aerosol source for sampling and characterization. The manifold tube has three openings (not shown), one to each chamber's initial stage to provide inlet flow to each chamber. Gas containing particles to be collected enters each chamber at the inlet, located at the bottom of the chamber, and flows upward through each collection stage, finally leaving the chamber at the outlet (outlets 16, 18, and 20 for chambers 11, 13, and 17 respectively). Although this embodiment provides for each chamber inlet at the bottom of the chamber and the aerosols to flow vertically upwards, it is clear that inlet 14 could be located at the top of device 10 and that each chamber inlet could also be located at the top of its chamber with aerosols flowing vertically downward.

Figure 4:
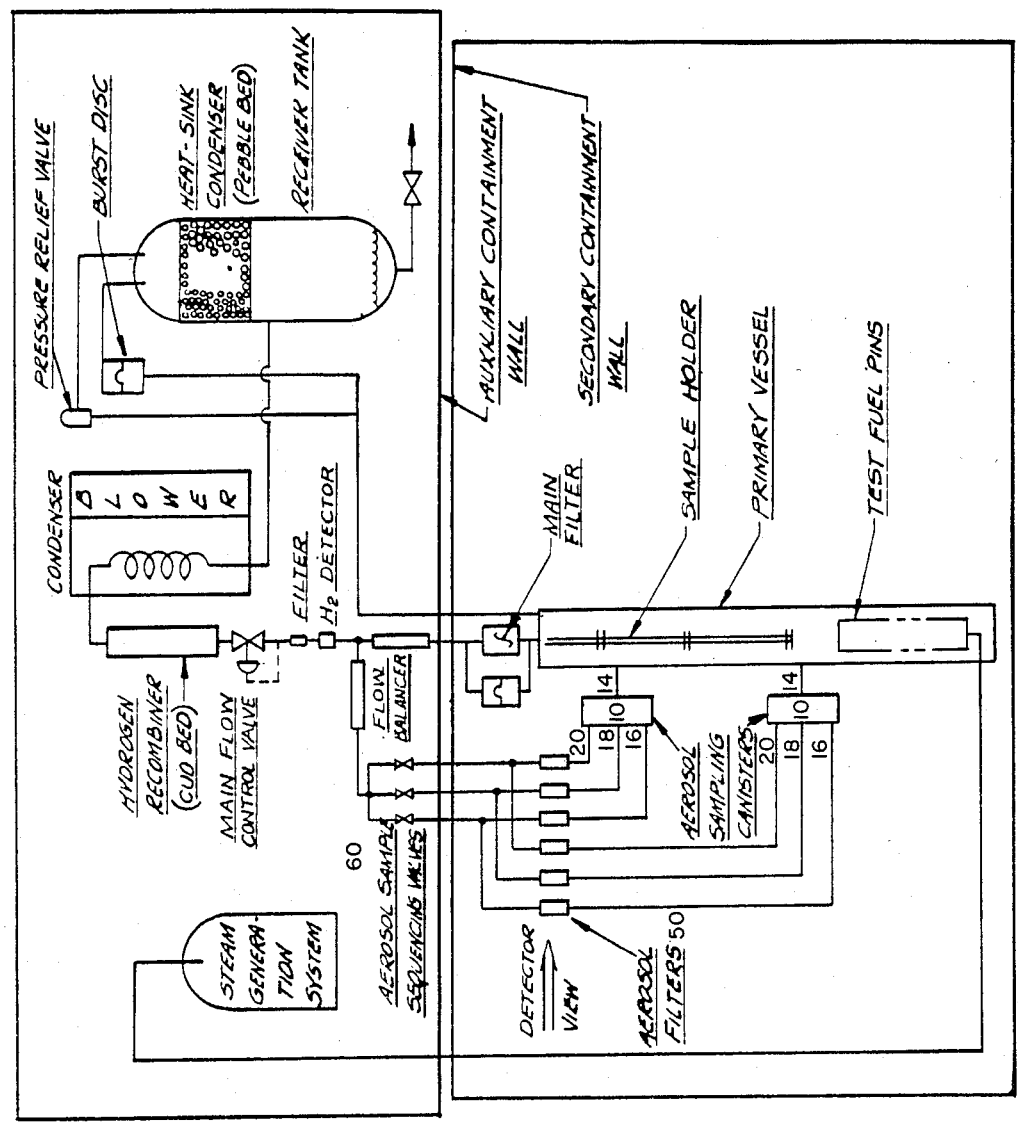
FIG. 4 is a schematic of an experiment to sample aerosols from a fuel pin failure using two of the sampling devices shown in FIG. 1.

In FIG. 4 sampling device 10 is shown schematically in an experimental set-up to sample aerosols from test fuel pins in a primary vessel. Input 14 receives the aerosols produced in the primary vessel. Outlets 16, 18, and 20 are connected through aerosol filters 50 to sequencing valves 60. The downstream end (outlets 16, 18, and 20) of the sampling aerosol flow is maintained at a pressure slightly less than that of the sampled gas. Opening one of the sequencing valves 60 permits the aerosol flow to enter the respective chamber from the manifold tube (connected to inlet 14) and to pass sequentially through its collection sections.

Figure 2:
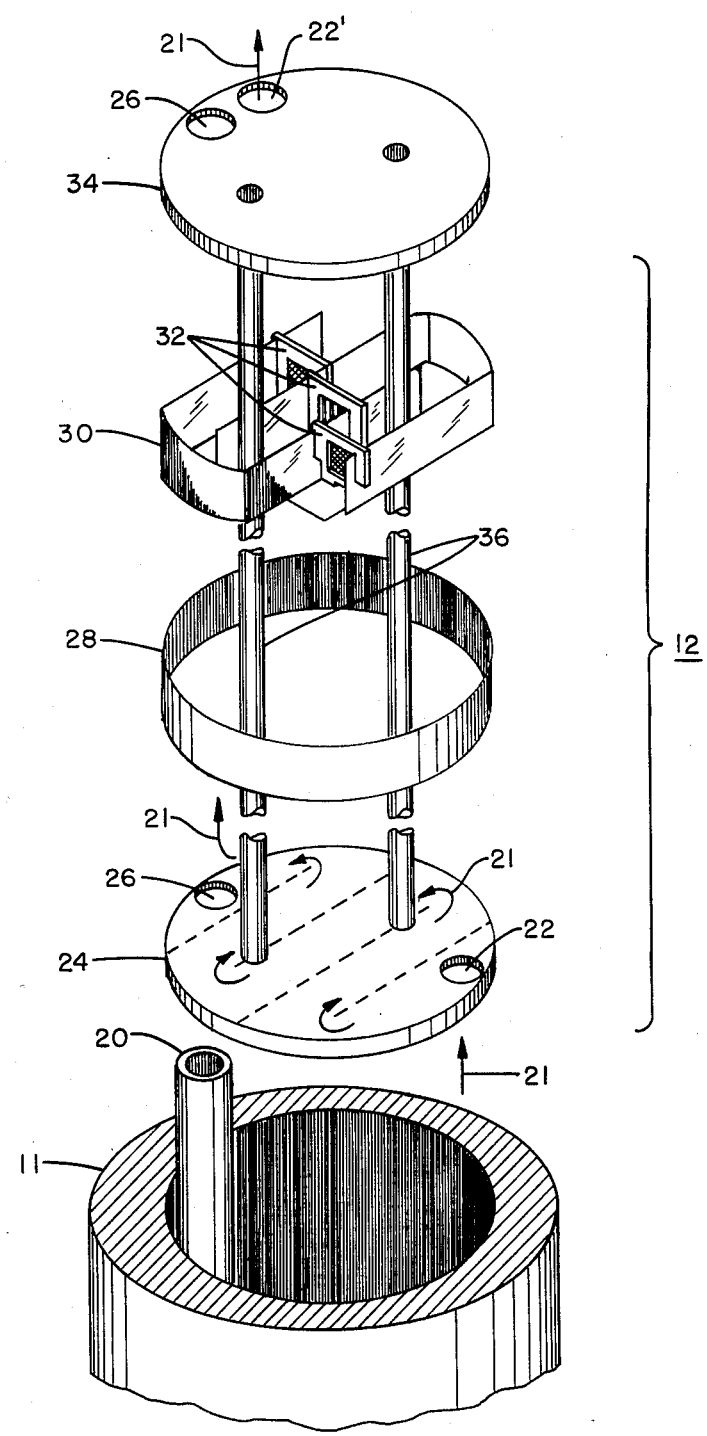
FIG. 2 is a detail of a collection stage from FIG. 1.

FIG. 2 shows a breakaway detail of a typical collection stage (12) in one of the chambers. Each collection stage consists of a separator plate (24 or 34) having two openings: opening 26 so that manifold tube 20 can pass through the stage and inlet opening 22 for receiving the aerosols from the section immediately beneath. Cylindrical separating wall 28 separates the collection stage from the canister body 11. Note that in this embodiment canister body 11 functions as the walls for the three chambers. An alternate embodiment would include a separate body for each chamber within the canister. In this alternate embodiment the manifold tube could be positioned inside or outside the canister body. Support rods 36 pass through all the stages and add rigidity to the stages. Within the collection stage is channel guide 30 mounted transverse to separator plate 24. Channel guide 30 provides support for the particle collection means 32 (positioned transverse to the flow path) and also defines a labyrinthine flow path within the section. The flow path 21 starts with aerosols entering opening 22, snaking in and out of the channel guide 30 and then travelling upward to the next collection stage where opening 22' of the next section is located at the opposite end of the channel guide. In this way it can be seen that the aerosols flow through a lengthy path beginning at inlet 14 through fourteen collection stages, snaking in and out of each stage, flowing upward to the last stage and exiting at outlet 16 (or 18 or 20). As the aerosols flow through each chamber within the canister, aerosols are collected on the various particle collection frames 32, settle by gravity on the separator plate 24 and collect on the channel guides 30 by diffusion. Although canister body 11 is shown to be cylindrical in shape, it is clear that any other convenient shape may be used.

Figure 3A:
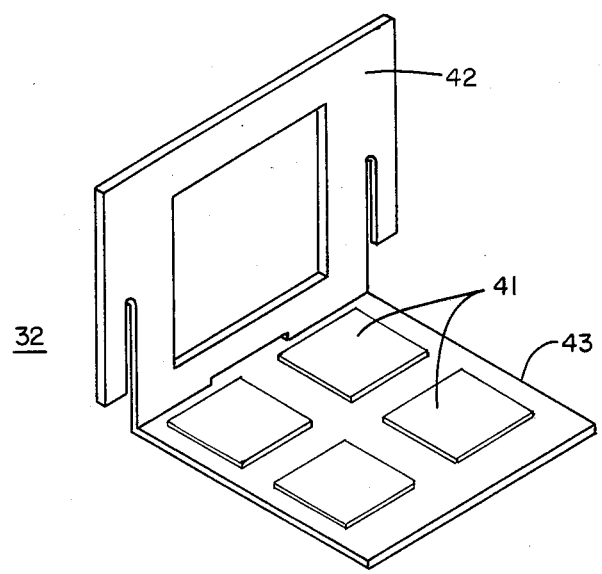
FIGS. 3A–3C are various particle collection means for use in the collection stages.
Figure 3B:
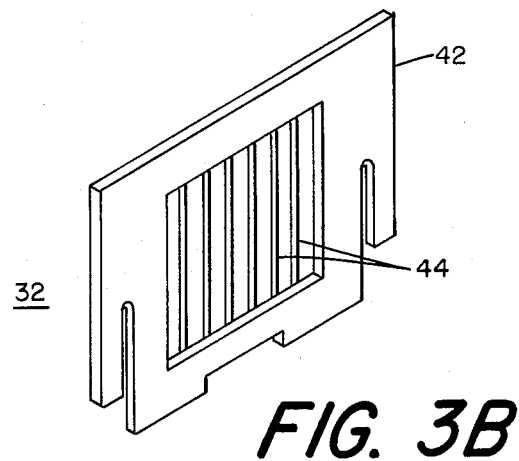
Figure 3C:
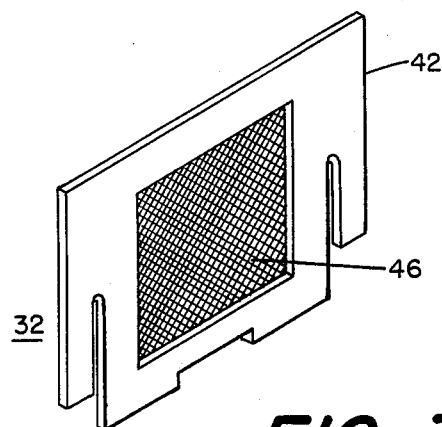

In FIGS. 3A–3C are shown three typical particle collection frames (32) suitable for use in aerosol sampling device 10. FIG. 3A shows an open frame 42 with horizontally positioned particle collection plate 43 suitable for collecting particles by gravitational settling. In gravitational settling, the aerosol flows down a horizontal flow path (parallel to the labryrinthine flow path) where heavier aerosols settle out first and lighter aerosols are carried farther downstream (in this case, vertically upward). Gravitational settling is used to collect particles whose diameters are greater than approximately one micron. Small coupons 41 of various metals can be affixed to the horizontal surface of the collection plate, yielding a metal coupon plate. Different metals (e.g., Zr-2, Ag, Pd, In-625, Ni, Pt, $Al_2O_3$, Fe, 316-SST, Ir, oxidized carbon steel, oxidized 316 SST) chemically interact with vapors passing over the coupons. By examining these coupons post-test, the type of vapors that passed over the coupon can be determined.

FIG. 3B shows frame 42 containing several fine wire impactors 44. In fine wire impaction, the impactor is a thin cylindrical obstruction placed in the flow path. Particles are either diverted around the wire or strike and adhere to the wires. Fine wire impaction is to be distinguished from flat plate impaction which involves collecting particles which impact the plate, which is placed directly in the flow path. Particles collected on impaction plates are generally weighed, whereas those collected on fine wire impactors are counted microscopically. Fine wire impactors are effective in collecting particles greater than approximately one micron in size.

Diffusion is used for particles that are so small they follow a Brownian movement within the flow stream and cannot be separated by gravitational settling or fine wire impaction. Diffusion battery screen 46 in FIG. 3C is used to collect particles from approximately 0.1 to down to 0.001 micron in size. A diffusion battery screen operates by the intermolecular attraction forces in the screen to attract the aerosols as they pass through.

The various collection frames described can be placed in any number, combination, or order desired within the collection stages. For example, lower stages may have only open frames for collection of heavier particles. The middle stages may have one or more open frames and fine wire impactors. Upper stages may preferably have one of each of the collection frames placed in order: gravitational settling first, fine wire impactor second, and diffusion screen last (downstream).

The fine wire impactors are particularly useful for determining the number concentration and size distribution of the aerosols at the impactor's location that can be collected with significant (>20%) efficiency and the relative changes in these quantities from one impactor location to another. The presence of certain volatile fission product vapors at the impactor's location can also be detected by choosing fine wires of different materials, e.g. silver which will react with iodine. In essence, in this manner the wires serve the same purpose as the metal coupon plates.

The fine wire impactors used on the source term experiments at the TREAT (Transient REeactor And Test) facility consist of a Type 316 stainless steel frame and four wires of various diameters and materials. The diameter range of wires having significant collection efficiencies over the range of gas velocities encountered (0.1 to 30 cm/s) is from 0.1 to 10 mils. Wire diameters actually used are 0.1, 0.2, 0.25, 0.5, 1, 3, 5, and 10 mil. Wire materials used are Pt, 70% Pt/30% Ir, Ni, Au, Ag, W, Pd, and Nichrome. All wires are affixed to the frames by laser microwelding. The collection efficiency for a fine wire is expressed in terms of the particle diameter-to-wire diameter stokes number, i.e., $$\eta(\% \text{ collected}) = Stk^2/(Stk+0.06)^2$$

where $Stk = C\rho_p d_p^2 U/9u_g d_w$, in which C is the Cunningham slip correction factor, $\rho_p$ the particle density, $d_p$ the particle diameter, U the gas velocity, $\mu_g$ the gas absolute viscosity and $d_w$ the wire diameter. From this equation, it can be seen that wires of smaller diameter are needed to obtain significant collection efficiencies at lower velocities.

The aerosol sampling device designed for TREAT can be removed remotely by an activated manipulator. A tab (not shown in FIG. 1 or 4) is provided at the upper end of the device for engagement by the manipulator. The canisters are also designed to be dismantled with the manipulator by removing a top closure cap and withdrawing the internals. After removing two nuts (attached to rods 36) the separate collection sections can then be dismantled sequentially from top to bottom. Once dismantled the various collector frames, channel guides, and separator plates are sent for particle analysis and counting. The overall path length for each chamber used at TREAT, having 14 collection stages, is approximately 325 cm. This is a significantly longer collection path than most commercial sampling instruments and offers the added advantages of collecting a wide range of particle sizes at relatively low velocities.

The embodiments of this invention in which an exclusive property or privilege is claimed are defined as follows:

1. Apparatus for sampling aerosols comprising:
a chamber having an inlet at one end and an outlet at the other end, said chamber including:
a plurality of vertically stacked, successive particle collection stages located within said chamber between said chamber inlet and chamber outlet and together with said chamber, defining a flow path from said chamber inlet, through successive collection stages, to said chamber outlet, each of said collection stages including:
a separator plate located within and extending across said chamber for separating that stage from the previous stage, said separator plate having an inlet opening extending therethrough, and
a channel guide, mounted transverse to said separator plate, defining a labyrinthine flow path from said inlet opening to the inlet opening of the next stage, and
a plurality of particle collection means supported by said channel guide and located within said labyrinthine flow path;
the particle collection means within the plurality of collection stages of the chamber including a combination of
collector plates for gravity separation,
fine wire impactors, and
diffusion battery screens.

2. The apparatus of claim 1 wherein said collector plate comprises a frame having an opening positioned transverse to said labyrinthine flow path and a flat plate for collection by gravitational settling connected to said frame and positioned substantially parallel to said labyrinthine flow path.

3. The apparatus of claim 2 further comprising one or more metal coupons affixed to said flat plate.

4. The apparatus of claim 3 wherein said coupons are formed of a material selected from the group consisting of Zr-2, Ag, Pd, In-625, 316-SST, Ni, Pt, $Al_2O_3$, Fe, oxidized 316-SST, and oxidized carbon steel.

5. The apparatus of claim 1 wherein said fine wire impactor comprises a frame having an opening and one or more fine wires fixedly placed across said opening.

6. The apparatus of claim 5 wherein said wires have a diameter of from 0.1 to 10 mils.

7. The apparatus of claim 5 wherein said wires are formed of a material selected from the group consisting of Pt, 70% Pt/30% Ir, Ni, Au, Ag, W, Pd, and Nichrome.

8. The apparatus of claim 1 further comprising means for injecting a stream of aerosols into said chamber inlet.

9. The apparatus of claim 8 wherein said means for injecting a stream provide for injection of the stream at a velocity of from approximately 0.1 to 30 cm/s.

10. The apparatus of claim 1 further comprising a canister and a manifold tube extending therethrough and a plurality of said chambers vertically stacked within said canister, wherein said manifold tube is connected to the inlet of each chamber.

* * * * *